(12) United States Patent
Bakshi et al.

(10) Patent No.: US 6,335,473 B1
(45) Date of Patent: Jan. 1, 2002

(54) METHOD FOR CONDUCTING EXOTHERMIC REACTIONS

(75) Inventors: Amarjit S. Bakshi; Timothy P. McGuirk; J. C. Gupta; Thomas Koval, all of Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/658,520

(22) Filed: Sep. 8, 2000

Related U.S. Application Data

(63) Continuation of application No. 08/276,637, filed on Jul. 18, 1994, now abandoned.

(51) Int. Cl.[7] .......................... C07C 41/01; C07C 41/09; C07C 2/08; C07C 41/06

(52) U.S. Cl. ...................... 568/697; 585/520; 585/526; 585/527

(58) Field of Search ..................... 568/697; 585/520, 585/526, 527

(56) References Cited

U.S. PATENT DOCUMENTS

| | | | |
|---|---|---|---|
| 4,504,687 A | 3/1985 | Jones, Jr. et al. | 568/697 |
| 4,950,803 A | 8/1990 | Smith, Jr. et al. | 568/697 |
| 5,003,124 A | 3/1991 | Smith, Jr. et al. | 585/526 |
| 5,190,730 A | 3/1993 | Smith, Jr. et al. | 422/109 |
| 5,248,837 A | 9/1993 | Smith, Jr. et al. | 568/697 |

*Primary Examiner*—Rosalynd Keys
(74) *Attorney, Agent, or Firm*—Kenneth H. Johnson

(57) ABSTRACT

A process for oligomerization of $C_4$ and C5 isoolefins or the etherification thereof with $C_1$ to $C_6$ alcohols wherein the reactants are contacted first in a partial liquid phase reactor (boiling point reactor) with a fixed bed acid cation exchange resin catalyst at an LHSV of 5 to 20, pressure of 0 to 400 psig and temperature of 120 to 300° F., at a pressure to maintain the reaction mixture at its boiling point whereby at least a portion but less than all of the reaction mixture is vaporized and the entire reaction stream is directed to a catalytic distillation column reactor for further reaction of the reactants, where the improvement is having a decoupling drum between the boiling point reactor and the catalytic distillation column reactor. The addition of a decoupler drum allows the reactors to operate at a pressure independent of each other.

16 Claims, 2 Drawing Sheets

METHOD FOR CONDUCTING EXOTHERMIC REACTIONS

This is a continuation of application Ser. No. 08/276,637, filed Jul. 18, 1994 now abandoned.

BACKGROUND OF THE INVENTION

1. Field of the Invention

The present invention relates to an improved process and apparatus for carrying out partially liquid phase reactions coupled with reactions in a catalytic distillation.

2. Related Art

It is well known that primary alcohols will react preferentially with the tertiary alkenes in the presence of an acid catalyst, for example, as taught in U.S. Pat. Nos. 3,121,124; 3,629,478; 3,634,534; 3,825,603; 3,846,088; 4,071,567; and 4,198,530.

U.S. Pat. Nos. 5,003,124 and 4,950,803 disclose a liquid phase process for oligomerization of $C_4$ and $C_5$ isoolefins or the etherification thereof with $C_1$ to $C_6$ alcohols in a boiling point fixed bed reactor (boiling point reactor) that is controlled at a pressure to maintain the reaction mixture at its boiling point which may be directly attached to a catalytic distillation reactor. The two reactors are then operated under a single pressure as determined by the overhead of the catalytic distillation tower.

The advantage of combining the two types of reactor is that the partial liquid phase reactor acts as a guard bed to the more expensive catalytic distillation column and converts a portion of the reactants to products, thus requiring less of the catalytic distillation structure. The conversions are usually around 85–90% while the catalytic distillation gives conversions of 97+%.

The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in a combination reactor-distillation structure as described in several U.S. Patents, namely U.S. Pat. Nos. 4,242,530; 4,250,052; 4,232,177; 4,302,356; 4,307,254; and 4,336,407.

For example, in this system and procedure, methanol and isobutene containing $C_4$ stream are continuously fed to the reactor/distillation column where they are contacted in the catalytic distillation structure. The methanol preferentially reacts with isobutene forming MTBE which is heavier than the $C_4$ components of the feed and the methanol, hence it drops in the column to form the bottoms. Concurrently, the unreacted $C_4$'s (e.g. n-butane, n-butenes) are lighter and form an overhead.

It is an advantage of the present system that the two reactors may be operated at different pressures. This and other advantages will become apparent from the following descriptions.

SUMMARY OF THE INVENTION

The present invention is an improvement that relates to a decoupling drum located between a boiling point fixed bed reactor and a catalytic distillation column. The decoupling drum allows a boiling point fixed bed reactor and a catalytic distillation column reactor to run at different operating pressures, thus allowing independent pressure control. The independent pressure control allows each reactor to be operated at their individual optimum conditions in order to maximize efficiency.

In one aspect the present invention is an improvement in the exothermic, partially liquid phase reaction of $C_4$ and $C_5$ isoolefins with themselves to form oligomers, preferably dimers, and with $C_1$ to $C_6$ alcohol to form ethers by contact in a boiling point reactor containing a fixed bed catalyst of acidic cation exchange resin, at a pressure to maintain the reaction mixture at its boiling point within the range of 120 degrees F. to 300 degrees F. whereby at least a portion but less than all of said reaction mixture is in the vapor phase said first reactor connected to a catalytic distillation column reactor having a fixed bed of catalyst, which also serves a distillation structure, wherein the improvement is the addition of a decoupling drum between said boiling fixed bed catalytic reactor and said catalytic distillation column whereby each reactor may be operated independently at different pressures.

The boiling point reactor is a substantial departure from the prior art for this type of reactor, where sufficient pressure was employed to maintain the entire reaction mixture in liquid phase.

A given composition, the reaction mixture, will have a different boiling point at different pressures, hence the temperature in the reactor is controlled by adjusting the pressure to the desired temperature within the recited range. The boiling point of the reaction mixture thus is the temperature of the exothermic heat of reaction which is dissipated by vaporization of the reaction mixture. For $C_4$ feeds where isobutene is >25 percent, a recycle is also provided so as to control the vaporization and temperature in the range desired for the process. The maximum temperature of any heated liquid composition will be the boiling point of the composition at a given pressure, with additional heat merely causing more boil up. The same principle operates in the present invention to control the temperature. There must be liquid present, however, to provide the boil up, otherwise the temperature in the reactor will continue to rise until the catalyst is damaged. In order to avoid exotherms which will vaporize all of the reaction mixture, as stated earlier, a recycle is necessary to limit the amount of vaporization and reactor temperature for the process. In this mode the process virtually can handle any concentration of isoolefins in the feed.

In another aspect the present invention is an improvement to a coupled liquid phase fixed bed boiling point reactor and a catalytic distillation column, wherein the improvement comprises a decoupling drum located therebetween. The decoupling drum allows the fixed bed boiling point reactor and the catalytic distillation column to run at different operating pressures, thus allowing independent pressure control. The independent pressure control allows the reactor and catalytic distillation column to individually operate at their optimum conditions in order to maximize efficiency and reduce the recycle requirements as some of the heat of reaction goes into vaporization. Other embodiments may include two fixed bed boiling point reactors in series, with the exit effluent from the second reactor connected to a decoupling drum before going to the catalytic distillation column reactor. The addition of the decoupler drum will allow the first boiling point reactor to operate at lower temperatures and pressures than when directly connected to the catalytic distillation column reactor. The lower pressure in the first boiling point reactor, results in lower temperature operation with more favorable conversion and selectivity. Any need for recycling the reactor effluent in the first boiling point reactor is reduced due to the increased efficiency. In addition, the increased efficiency allows for a smaller size boiling point reactor resulting in lower equipment and operating costs.

The present reaction scheme is the preferred operation on streams containing large amounts of the isoolefin, however, feed to the reaction will need to be preheated. Since high concentrations of isoolefin (25 to 60 wt. % for $C_4$ feed) provide a great exotherm, hence liquid recycle is used as a diluent to control the temperature in the reactor so as to provide limited vaporization. In any event it may be necessary to preheat the feed to the reaction such that temperature of the reaction, i.e., the boiling point of the reaction mixture (feed temperature plus exotherm) is in the range of 120° F. to 300° F., which represents the desirable range for the equilibrium reactions at a pressure in the range of 0 to 400 psig.

The catalyst bed in the liquid phase boiling point reactor may be described as a fixed continuous bed, that is, the catalyst is loaded into the reactor in its particulated form to fill the reactor or reaction zone, although there may be one or more such continuous beds in a reactor, separated by spaces devoid of catalyst. The catalyst bed in the distillation reaction column reactor is in such a form as to act as both the catalyst for the reaction and distillation structure for the fractional distillation.

DETAILED DESCRIPTION OF THE INVENTION

Figure 1:
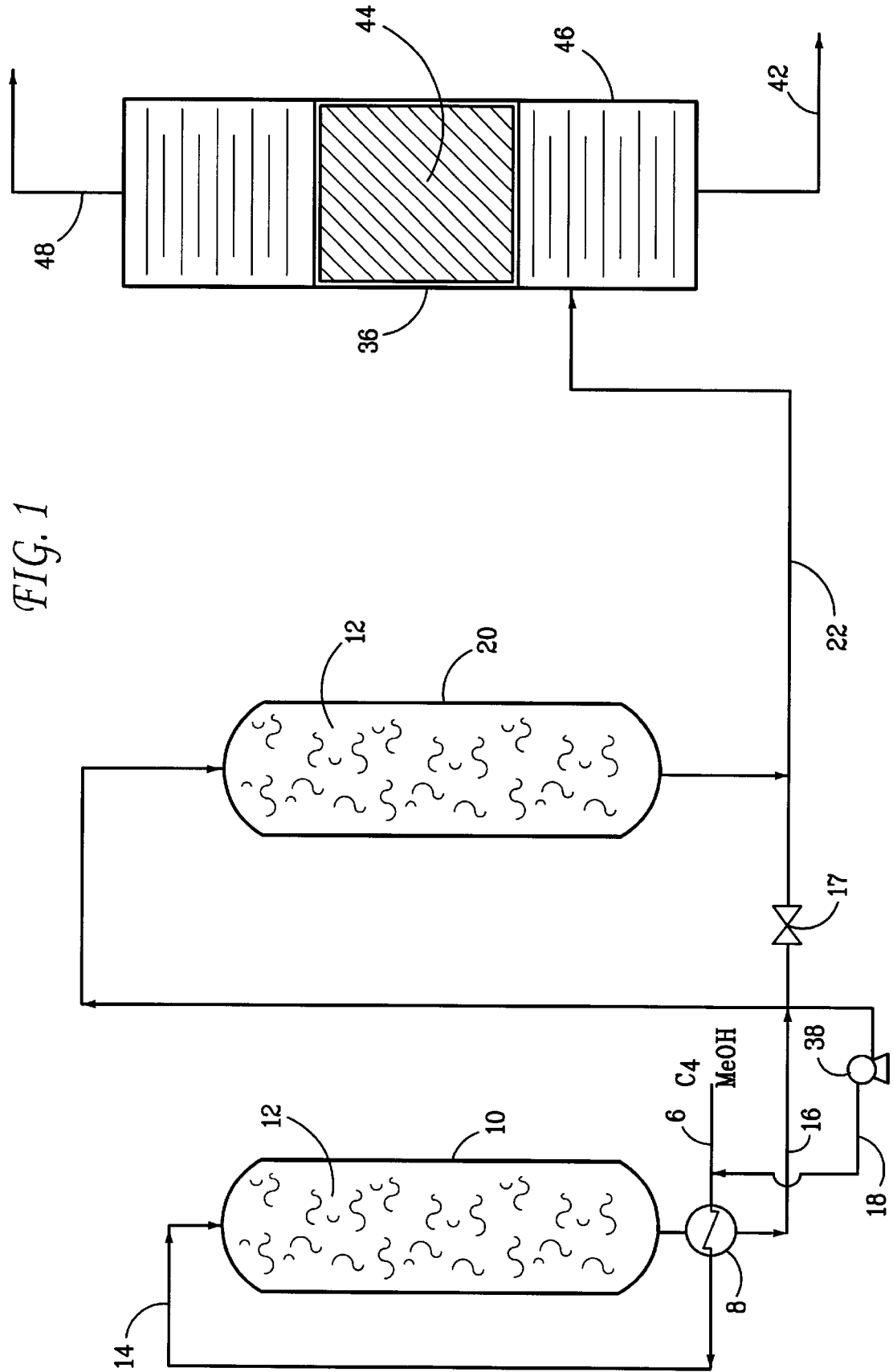
FIG. 1 shows the heat of the reaction recovered by preheating the feed to the boiling point reactor, with the reactor effluent going to a catalytic distillation column reactor.

The temperature in the boiling point reactor is controlled by the combination of recycle and vaporization and is easily provided by pressure control. The temperature in the boiling point reactor and catalyst bed is limited to the boiling point of the mixture present at the pressure applied, notwithstanding the magnitude of the exotherm. A small exotherm may cause only a few percent of the liquid in the boiling point reactor to vaporize whereas a large exotherm may cause 30–90% of the liquids to vaporize. It is preferred that vaporization in the range of 10 wt. percent, hence recycle and vaporization are used to control the temperature which is easily provided by pressure control. The temperature, however, is not dependent on the amount of material vaporized but the composition of the material being vaporized at a given pressure. That "excess" heat of reaction merely causes a greater boil up (vaporization) of the material present.

Although the reaction is exothermic, it is necessary to initiate the reaction, e.g., by heating the feed to the reactor. In prior reactors, such as the tubular reactors, the temperature of the reaction (bed) may be controlled with the heat exchange medium; i.e., either adding or removing heat or removing heat as required. In any event, once the reaction is initiated an exotherm develops and must be controlled to prevent a runaway reaction or damage to the catalyst.

The reaction product (ethers, dimers, unreacted feed) of the partial liquid phase boiling point reactor in the present invention is at a higher temperature than the feed into the reactor with a portion being vapor and a portion liquid. The boiling point reactor is operated at a high liquid hourly space velocity (4–20 LHSV, preferably 5–20) to avoid the reverse reaction and polymerization of the olefins present in the feed. Under these conditions high conversion of feeds are obtained, e.g., 80–90% conversion and somewhat lower conversions for stream containing higher concentrations of the isoolefins, e.g. containing 25 to 60 weight percent isoolefins.

Thus, it may be desirable to have two and possibly more of the present liquid phase boiling point reactors in series to obtain higher conversions of the isoolefins. In such a case the product from the first boiling point reactor will normally be cooled by heat exchange to obtain the desired temperature in the second boiling point reactor.

Conveniently the feed to the first boiling point reactor is used to cool the product from the first boiling point reactor prior to its entry into the second boiling point reactor, hence the heat of reaction supplies some of the heat necessary to initiate the reaction in the first boiling point reactor. Hence, the boiling point reactor or reactors can be operated in a substantially adiabatic manner.

The product from either a single partial liquid phase boiling point reactor or a series of such reactors operated quasi-isothermally as taught here is fed to a catalytic distillation column reactor through a decoupler drum which also provides recycle liquid to the boiling point reactor to provide a heat sink.

Another advantage of the combination is that the small partial liquid phase bed can serve as a guard bed for the distillation column reactor bed since catalyst poisons (metal ions, amines and sulfur compounds) even if present in parts per billion will deactivate the acidic cation exchange resin in time. The small guard bed can be easily and less expensively replaced as it is deactivated while the life of the catalytic distillation bed may be extended several years.

An improvement in operation is obtained by adding a decoupling drum between the fixed bed boiling point reactor and the catalytic distillation column reactor. The decoupler drum allows the fixed bed boiling point reactor and the catalytic distillation column to operate at different pressures. The decoupler drum is desirable to reduce the operating temperature and pressure in the reactors and the liquid/vapor is condensed in an exchanger before it is sent to decoupler. The optimum pressure for the fixed bed boiling point reactors is around 45–100 psig, while the catalytic distillation column reactor optimum pressure is 100–120 psig.

The catalytic distillation uses an acid catalyst such as an acidic cation exchange resin in a form to serve as the distillation structure. This has the advantage of further reacting the residual isoolefins while fractionating the reaction product concurrently to produce even higher conversion of the isoolefins. This combination has a further advantage in that both catalyst beds, i.e., the fixed partial liquid phase boiling point reactor and the catalytic distillation column reactor can be relatively small compared to the use of either bed alone when used to obtain the same level of isoolefin conversion obtained by the combination.

A container employed to hold the catalyst particles may have any configuration, such as the pockets disclosed in the commonly assigned patents above, or the container may be a single cylinder, sphere, doughnut, cube, tube or the like.

Each unit containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus, desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like, each such larger component may be individually intimately associated with or surrounded by the spacing component as described above.

It is not essential that the spacing component entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the mole sieve or cation exchange resin particles into a plurality of pockets in a cloth belt which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred.

Catalysts preferred for the present process are cation exchangers which contain sulfonic acid groups and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl cholorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide after the reaction so that it still contains 10 to 50% free sulfur trioxide.

The resulting products preferably contain an average of 1.3 to 1.8 sulfonic acid groups per aromatic nucleus. Particularly suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles form 0.15 mm up to about 1 mm may be employed. The finer catalysts provide high surface area but also result in high pressure drops throughout the reactor. The macroreticular form of these catalysts is preferred because of the much larger surface area exposed and the limited swelling which all of these resins undergo in a non-aqueous hydrocarbon medium.

Similarly, other acid resins are suitable such as perfluorosulfonic acid resins which are copolymers of sulfonyl fluorovinyl ethyl and fluorocarbon and described in greater detail in DuPont "Innovation", volume 4, No. 3, Spring 1973 or the modified forms thereof as described in U.S. Pat. Nos. 3,784,399; 3,770,567 and 3,849,243.

The resin catalyst is loaded into a partial liquid phase boiling point reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

For the oligomerization and etherification reactions, the feed may be a $C_4$ or $C_5$ containing stream, for example, a $C_4$ or $C_5$ refinery cut, although a mixed stream could be employed. In addition to $C_4$, such a $C_4$ stream my contain small amounts of $C_3$ and $C_5$ and a $C_5$ will contain small amounts of $C_4$ and $C_6$ depending on the precision of the refinery fractionation.

Isobutene is the $C_4$ isoolefin and it dimerizes to produce diisobutene. Some higher oligomers are produced as well as some codimers with n-butenes that are normally present in a $C_4$ but in the presence of methanol little dimer is produced. The dimerization is the preferential reaction in absence of methanol because the two most reactive molecules are combining. Higher polymers result from the continued contact of the dimer with isobutene in the presence of the catalyst. At the high LHSV (low resident time) employed for the present reaction, in the presence of methanol, little polymer is formed.

Isoamylene has two isomers, i.e., 2-methyl butene-1 and 2 methyl butene-2, both of which are normally present in a $C_5$ stream. Both are highly reactive and the dimer product is a mixture of the three possible dimers.

Both the isobutene and isoamylene preferentially react with alcohols in the presence of an acid catalyst, hence only small amounts of dimer or other oligomerization products are produced when the etherification is carried out.

The $C_1$ to $C_6$ alcohol for the etherification may be fed to the reactor with the hydrocarbon stream or by a separate feed. The methanol is preferably fed at the upstream end of the reactor to inhibit oligomerization of the olefins and to preferentially react with more reactive isoolefins to form ethers.

The alcohol, e.g., methanol may be and is preferably present in a stoichiometric amount of the isoolefin present although an excess of up to 10%, may be desirable. In addition, slightly less than a stoichiometric amount may be employed. It should be appreciated that the skilled chemist will optimize the proportions and precise condition for each particular piece of equipment and variation in catalyst once the basic invention is comprehended. The alcohols employed are those having 1 to 6 carbon atoms. Preferred are those having one hydroxyl group. Preferred alcohols include methanol, ethanol, propanol, n-butanol, tertiary butanol, 1-pentanol, 2-pentanol, 3-pentanol, 1-hexanol, 2-hexanol, 3-hexanol, cyclopentanol and hexanol. A preferred grouping of alcohols are those having 1 to 4 carbon atoms and one hydroxyl group.

The alcohols may be used alone or in mixtures of any proportion to produce highly complex ether products having unique properties as octane improvers for gasoline or as solvents.

The reaction in the fixed bed boiling point reactor is primarily a liquid phase reaction, but unlike all other known liquid oligomerizations and etherifications reactions carried out in this manner, no attempt is made in the present process to maintain a completely liquid phase. Since the reaction is exothermic, the pressure in the reactor is adjusted to maintain the desired temperature together with recycle which allows some portion of the material to be vaporized. The reactor may be said to run in a quasi-isothermal manner.

EXAMPLE 1

Referring to FIG. 1, a simple reactor 10, packed with acidic cation exchange resin catalyst 12 is shown.

The feed was a $C_4$ cut (from steam cracker or dehydrogenation plant or mixed from refinery and steam cracker) admixed with methanol 6 and entered the reactor via line 14. The feed had been preheated to 110–150° F. by cross exchanging the line 14 with the reactor exit line 16 in the preheater 8. After the indirect contact of the reaction product and feed in the preheater 8 the cooled product exits via line 16.

A portion of product stream 16 proceeds to a second reactor 20 for further conversion of the reactants and another portion is recycled to line 14 via line 18 by pump 38. The products of the second reactor 20 exit via line 22 and proceed to the catalytic distillation column 36. Alternatively, the second partial liquid phase reactor may be omitted and the product stream (mixed vapor/liquid) from the first boiling point reactor sent directly into line 22 via valve 17. The reactors 10, 20 and the catalytic distillation column reactor 36 containing catalytic distillation packing 44 and standard distillation trays above 40 and below 46 run at the same system pressure. Results illustrating a typical operation are set out in TABLE I. The ether product is recovered as bottoms 42 and unreacted components are taken overhead at 48. Reflux and reboiling (not shown) may be used as known in the art. The results provided here are from only one combined fixed bed reactor and catalytic distillation, as this is the arrangement normally used.

EXAMPLE 2

Figure 2:
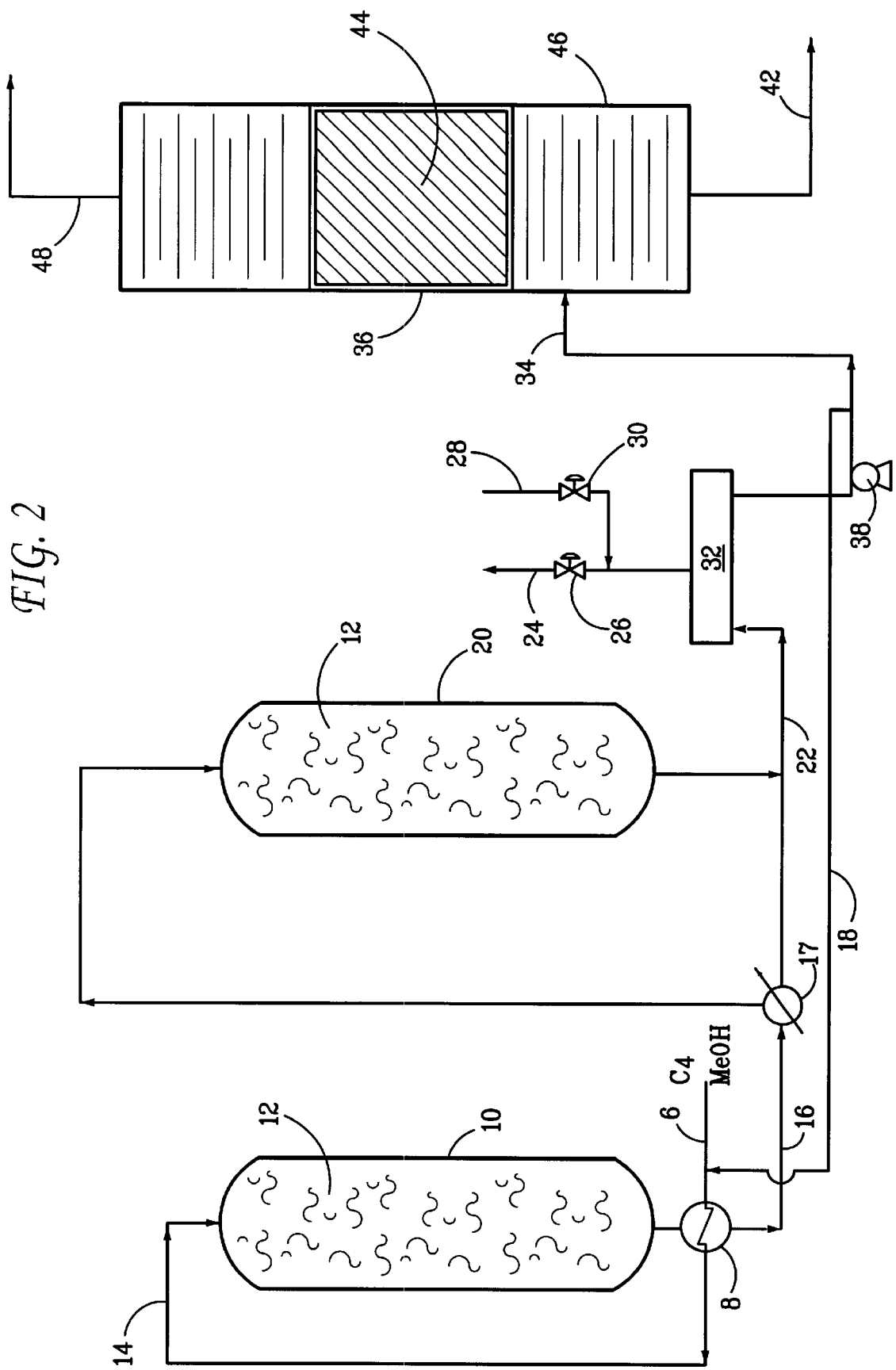
FIG. 2 shows the addition of a decoupling drum between the boiling point reactor and the catalytic distillation column reaction described in FIG. 1.

FIG. 2 represents an identical system as that illustrated in FIG. 1, with the addition of a decoupler drum 32.

The feed was steam cracker or dehydrogenation based $C_4$ cut admixed with methanol and entered the reactor via line 14. The feed had been preheated to 110–150° F. by cross exchanging the line 14 with the reactor exit line 16 in the preheater 8. After the indirect contact of the reaction product and feed in the preheater 8 the cooled product exits via line 16.

The portion of product stream 16 proceeds to a second reactor 20 for further conversion of the reactants and another portion is recycled to line 14 via line 18 by pump 38. The products of the second reactor 20 exit via line 22 and proceed to the decoupler drum 32 where the system pressure for the first reactor 10 and second reactor 20 is controlled independently from the catalytic distillation column reactor 36. The decoupling drum 32 controls the pressure at the desired pressure setpoint by way of a standard pressure controller. The pressure controller when necessary to increase pressure in the decoupler drum 32, opens the pad valve 30 to allow nitrogen via line 28 to flow into the decoupler drum 32. When necessary to decrease the pressure in the decoupler drum 32, the vent valve 26 is opened to vent through the vent line 24. The feed from the decoupler goes via pump 38 to column 36 and a portion may be recycled to reactor 10 via line 18.

The decoupling drum allows the reactor system to operate at an optimum pressure in order to maximize yields and conversion. Independent operation of the reactors and the catalytic distillation column has been found to be desirable.

Operated in this manner the feed to boiling point reactor 10 is at a temperature near the exotherm, hence the reactor is operating under near adiabatic conditions.

The catalytic distillation column reactor 36 where the residual isoalkene is reacted with residual methanol (or added methanol to produce extremely high conversions of the isoalkene in a single pass through the system (e.g. 95%+). The packing in a catalytic distillation column is described in the above noted patents, but briefly it has been found that placing the resin beads into a plurality of pockets in a cloth belt which is supported in the distillation column reactor by open mesh knitted stainless steel wire by twisting the two together, allows the requisite flows, prevents loss of catalyst, allows for the normal swelling of the beads and prevents the breakage of the beads through mechanical attribution.

The cloth may be of any material which is not attacked by the hydrocarbon feed or products under the conditions of the reaction. Cotton or linen are useful, but fiber glass cloth or "Teflon" cloth are preferred. A preferred catalyst system comprises a plurality of closed cloth pockets arranged and supported in said distillation column reactor and supported in said distillation column reactor by wire mesh intimately associated therewith.

The particular catalytic material may be a powder, small irregular fragments or chunks, small beads and the like. The particular form of the catalytic material in the cloth pockets is not critical so long as sufficient surface area is provided to allow a reasonable reaction rate. This sizing of catalyst particles can be best determined for each catalytic material (since the porosity or available internal surface area will vary for different materials, and, of course, affects the activity of the catalytic material).

For oligomerizations and etherifications, the catalyst is the same type, an acidic cation exchanged resin, used in the boiling point reactors.

It should be appreciated that the combination mechanism of allowing excess heat of reaction to create boil up and reactor effluent recycle has been employed in both the continuous bed reactors. Although as noted above, fixed bed reactors have been disclosed to operate in different processes in a quasi-isothermal manner the operation of a liquid phase etherification in this manner is in direct conflict with all of art on the subject.

In the second example of the present invention given here, approximately 10–30% of the feed in the boiling point reactor was vaporized. In Examples 1 and 2 the product 16 leaving the heat exchanger was all liquid, however, in some operations according to the present invention, depending on the temperature and composition of stream 16, a portion may still be in the vapor state which should be condensed in a second heat exchanger before entering the second boiling point reactor, if any.

The heat exchanger 8 should be sized, such that an amount of heat equal to the heat of reaction in reactor 10 is allowed to pass through, otherwise additional exchanges should be provided so that the heat in the reactor should not build up.

In the oligomerization, just as in the etherification, the tertiary olefins are more reactive and tend to form oligomers, primarily dimers, e.g., diisobutene, some higher oligomers and some codimers with normal olefins. The oligomerizations are run under the same general conditions as the etherifications with the oligomer products being the heavier component of the product stream. In fact, it may be desirable in some operations to switch between the two reactions, by adding or withholding the alcohol as desired.

The pressure operation for each reactor is independently adjusted in Example 2 to give the optimum results for each reactor. The results of such an operation using the same feed as for Example 1 are set out in TABLE II. As only one fixed boiling point reactor and catalytic distillation column reactor are normally used, the results of the singlely paired reactors operation are being provided.

What is claimed is:

1. A process for the exothermic reaction of $C_4$ or $C_5$ olefins with themselves or $C_1$ to $C_6$ alcohols to form oligomers or ethers by contacting a feed stream containing up to 60 weight percent of said olefins or a mixture of said olefins with said alcohols with a fixed bed catalyst comprising an acid cation exchange resin at a temperature in the range of 120° F. to 300° F. in a partial liquid phase reactor to form a reaction mixture containing oligomers, ethers or mixtures thereof, said reactor operating at a pressure to maintain said reaction mixture in said reactor at its boiling point within the range of 120° F. to 300° F. whereby at least a portion but less than all of said reaction mixture is vaporized and all of said reaction mixture is recovered as a single stream and feeding said stream to a decoupling drum and feeding said stream from said decoupling drum to a distillation column reactor containing catalyst in the form of a distillation structure whereby the pressure of said partial liquid phase reactor and said catalytic distillation column reactor are controlled independently at different pressures to optimize the operation of each reactor independently.

2. The process according to claim 1 wherein a predominantly $C_4$ hydrocarbon feed stream from 1 to 60 weight percent isobutene is contacted with said fixed bed catalyst in said partial liquid phase reactor.

3. The process according to claim 2 wherein the pressure in the partial liquid phase reactor is in the range of 0 to 400 psig and the LHSV of said stream is in the range of 5 to 20.

4. The process according to claim 3 wherein said reaction mixture contains unreacted $C_4$ hydrocarbon and a predominant of diisobutene.

TABLE 1

Example 1

| Conditions | Line 6 | | Line 18 | | Line 14 | | Line 22 | | Line 42 | | Line 48 | |
|---|---|---|---|---|---|---|---|---|---|---|---|---|
| Temp., ° F. | — | | 130 | | 120 | | 130 | | 100 | | 120 | |
| Press., psig | 140 | | 125 | | 125 | | 115 | | 100 | | 100 | |
| LHSV 4.0 | | | | | | | | | | | | |
| Composition | lbs/hr | wt. % | lbs/hr | wt. % | lbs/hr | wt. % | lbs/hr | wt. % | lbs/hr | wt. % | lbs/hr | wt. % |
| Isobutene | 34 | 34 | 16 | 4 | 50 | 10 | 4 | 4 | — | — | — | 1 |
| Other $C_4$'s | 45 | 45 | 176 | 44 | 221 | 44 | 44 | 44 | — | 0.1 | 44 | 95.5 |
| Methanol | 21 | 21 | 16 | 4 | 37 | 7 | 4 | 4 | — | 0.1 | 2 | 3.5 |
| MTBE | — | — | 192 | 48 | 192 | 39 | 48 | 48 | 54 | 99.8 | — | — |
| Conversion of isobutene- | | | | | | | 90 | | | | 99 | |
| Recycle To Feed 4.0 | | | | | | | | | | | | |

TABLE II

Example 2

| Conditions | Line 6 | | Line 18 | | Line 14 | | Line 22 | | Line 42 | | Line 48 | |
|---|---|---|---|---|---|---|---|---|---|---|---|---|
| Temp., ° F. | — | | 130 | | 120 | | 130 | | 100 | | 120 | |
| Press., psig | 100 | | 85 | | 85 | | 65 | | 100 | | 100 | |
| LHSV 6.0 | 110 | | | | | | | | | | | |
| Composition | lbs/hr | wt. % | lbs/hr | wt. % | lbs/hr | wt. % | lbs/hr | wt. % | lbs/hr | wt. % | lbs/hr | wt. % |
| Isobutene | 34 | 34 | 10 | 4 | 34 | 13 | 14 | 4 | — | — | — | 1 |
| Other $C_4$'s | 45 | 45 | 110 | 44 | 155 | 44 | 154 | 44 | — | 0.1 | 44 | 95.5 |
| Methanol | 21 | 21 | 10 | 4 | 31 | 9 | 14 | 4 | — | 0.1 | 2 | 3.5 |
| MTBE | — | — | 120 | 48 | 120 | 34 | 168 | 48 | 54 | 99.8 | — | — |
| Conversion of isobutene- | | | | | | | 90 | | | | 99 | |
| Recycle To Feed 2.5 | | | | | | | | | | | | |

5. The process according to claim 4 wherein said feed stream is preheated by indirect heat exchange contact with the reaction mixture from said reactor.

6. The process according to claim 1 wherein a predominantly $C_5$ hydrocarbon feed stream containing from 1 to 60 weight percent isoamylene is contacted with said fixed bed catalyst.

7. The process according to claim 6 wherein the pressure in the reactor is in the range of 0 to 400 psig and the LHSV of said stream is in the range of 2 to 20.

8. The process according to claim 7 wherein said reaction mixture contains unreacted $C_5$ hydrocarbon and a predominant amount of dimers of isoamylene.

9. The process according to claim 8 wherein said feed stream is preheated by indirect heat exchange contact with the reaction mixture from said reactor.

10. The process according to claim 1 wherein said feed stream is preheated prior to contact with said catalyst.

11. The process according to claim 2 comprising a $C_1$ to $C_6$ alcohol reacted with said isobutene.

12. The process according to claim 11 wherein said alcohol comprises methanol.

13. The process according to claim 11 wherein said alcohol comprises ethanol.

14. The process according to claim 6 comprising a $C_1$ to $C_6$ alcohol reacted with said isoamylene.

15. The process according to claim 14 wherein said alcohol comprises methanol.

16. The process according to claim 14 wherein said alcohol comprises ethanol.

* * * * *